US 9,932,878 B2

(12) United States Patent
Zhang

(10) Patent No.: US 9,932,878 B2
(45) Date of Patent: Apr. 3, 2018

(54) PARTICULATE MATTER SENSOR

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 132 days.

(21) Appl. No.: 15/018,637

(22) Filed: Feb. 8, 2016

(65) Prior Publication Data

US 2017/0226916 A1    Aug. 10, 2017

(51) Int. Cl.
| | |
|---|---|
| *F01N 11/00* | (2006.01) |
| *F01N 13/00* | (2010.01) |
| *F01N 3/00* | (2006.01) |
| *F01N 3/021* | (2006.01) |
| *G01N 15/06* | (2006.01) |
| *G01N 15/10* | (2006.01) |
| *G01M 15/10* | (2006.01) |
| *G01N 15/00* | (2006.01) |

(52) U.S. Cl.
CPC .......... *F01N 11/007* (2013.01); *F01N 13/008* (2013.01); *G01M 15/102* (2013.01); *G01N 15/0656* (2013.01); *F01N 2560/05* (2013.01); *G01N 2015/0046* (2013.01)

(58) Field of Classification Search
CPC . F01N 3/00; F01N 3/021; F01N 11/00; F01N 11/007; F01N 13/00; F01N 13/008; F01N 2560/05; G01M 15/102; G01N 15/06; G01N 15/0656; G01N 15/10; G01N 2015/0046
See application file for complete search history.

(56) References Cited

U.S. PATENT DOCUMENTS

| | | | |
|---|---|---|---|
| 8,375,691 B2 | 2/2013 | Klippert et al. | |
| 8,756,913 B2* | 6/2014 | Liu | F01N 3/2066 422/82.01 |
| 2011/0232268 A1* | 9/2011 | Nelson | G01N 15/0656 60/276 |
| 2012/0312074 A1* | 12/2012 | Allmendinger | G01N 15/0656 73/23.31 |
| 2015/0355066 A1* | 12/2015 | Zhang | G01N 15/0656 73/23.31 |
| 2016/0131013 A1* | 5/2016 | Yi | F01N 13/08 60/276 |
| 2016/0160721 A1* | 6/2016 | Zhang | F01N 3/033 60/274 |
| 2017/0081999 A1* | 3/2017 | Lee | F01N 3/035 |

OTHER PUBLICATIONS

Zhang, Xiaogang, "Exhaust Flow Device," U.S. Appl. No. 14/706,650, filed May 7, 2015, 47 pages.
Zhang, Xiaogang, "System for a Urea Mixer," U.S. Appl. No. 14/945,122, filed Nov. 18, 2015, 30 pages.

* cited by examiner

*Primary Examiner* — Nguyen Ha
(74) *Attorney, Agent, or Firm* — Julia Voutyras; McCoy Russell LLP

(57) ABSTRACT

Methods and systems are provided for sensing particulate matter in an exhaust system of a vehicle. An example system comprises a particulate matter sensor inside a tube configured to receive a portion of exhaust gas in an exhaust passage.

20 Claims, 4 Drawing Sheets

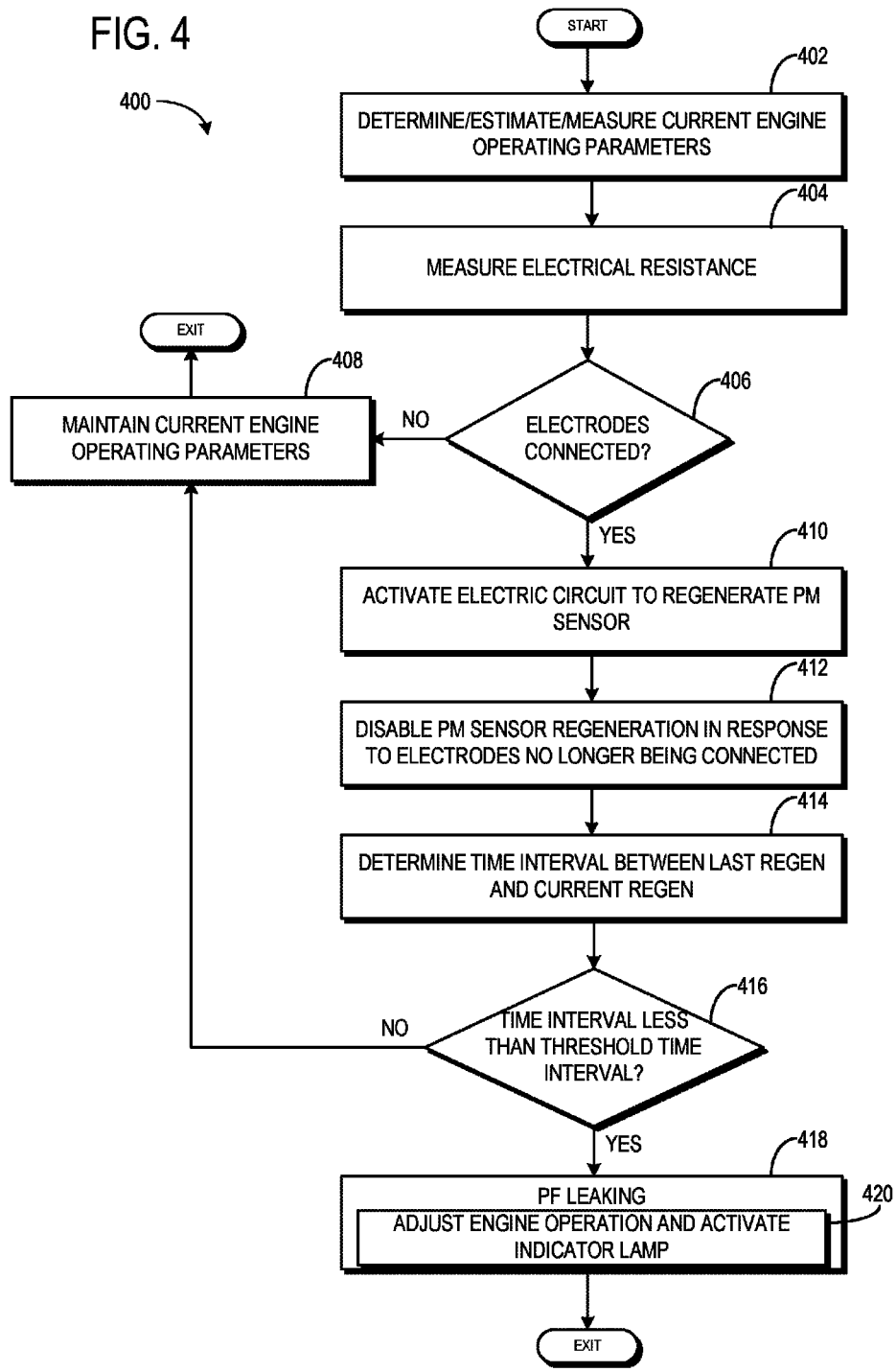

PARTICULATE MATTER SENSOR

FIELD

The present description relates generally to a particulate matter sensor assembly.

BACKGROUND/SUMMARY

Engine emission control systems may utilize various exhaust sensors. One example sensor may be a particulate matter sensor which indicates particulate matter mass and/or concentration in the exhaust gas. In one example, the particulate matter sensor may operate by accumulating particulate matter over time and providing an indication of the degree of accumulation as a measure of exhaust particulate matter levels.

Particulate matter sensors may correlate a measured change in electrical conductivity (or resistivity) between a pair of electrodes placed on a substrate surface of the sensor with the amount of particulate matter deposited between the electrodes. Particulate matter sensors may encounter problems with non-uniform deposition of soot on the sensor due to a bias in flow distribution across the surface of the sensor. Further, particulate matter sensors may be prone to contamination from an impingement of water droplets and/or larger particulates present in the exhaust gases. This contamination may lead to errors in sensor output.

Other attempts to address particulate matter sensor performance include guiding a portion of exhaust toward the particulate matter sensor. One example approach is shown by Liu et al. in U.S. Pat. No. 8,756,913. Therein, a pair of intersecting tubes are located along an exhaust passage with a sensor located in an upper portion of the exhaust passage fluidly coupled to an axial tube of the pair of tubes. The tubes are configured to receive exhaust gas from a variety of locations within the exhaust passage to increase an accuracy of data provided by the sensor.

However, the inventors herein have recognized potential issues with such systems. As one example, the pair of tubes may conduct large particulate matter and/or water droplets onto the sensor. This may decrease a reliability of data provided by the sensor with regards to PF degradation.

The inventors herein have recognized the above issues and identified an approach to at least partly address both the general issues as well as particular issues with Liu. In one example, the issues described above may be addressed by a system comprising two fully intersecting tubes fluidly coupled to an outer circular tube, and where the intersecting and circular tubes are fluidly coupled to a sensor via a bent tube (an L- or C-shaped tube, for example) in an upstream direction relative to exhaust flow. In this way, a likelihood of large particulates and water droplets flowing to the sensor is decreased.

As one example, the circular tube is radially spaced away from interior surfaces of an exhaust pipe. The intersecting tubes and the outer circular tube comprise inlets facing a direction of incoming exhaust flow. The inlets are configured to admit exhaust flow into a common interior passage of the circular and intersecting tubes. Exhaust gas in the interior space may flow into the L-shaped tube in an upstream direction opposite a direction of incoming exhaust flow. This may decrease and/or prevent large particulates and/or water droplets from flowing to a PM sensor located in an upper portion of the L-shaped tube due to a greater momentum of the large particulates and/or water droplets carrying them to a back wall of the interior space. Overall, functioning of the PM sensor may be improved and may be more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2-3 are shown approximately to scale, although other relative dimensions may be used without departing from the scope of the present disclosure.

FIG. 4 shows a method for determining a condition of a particulate filter.

DETAILED DESCRIPTION

Figure 1:
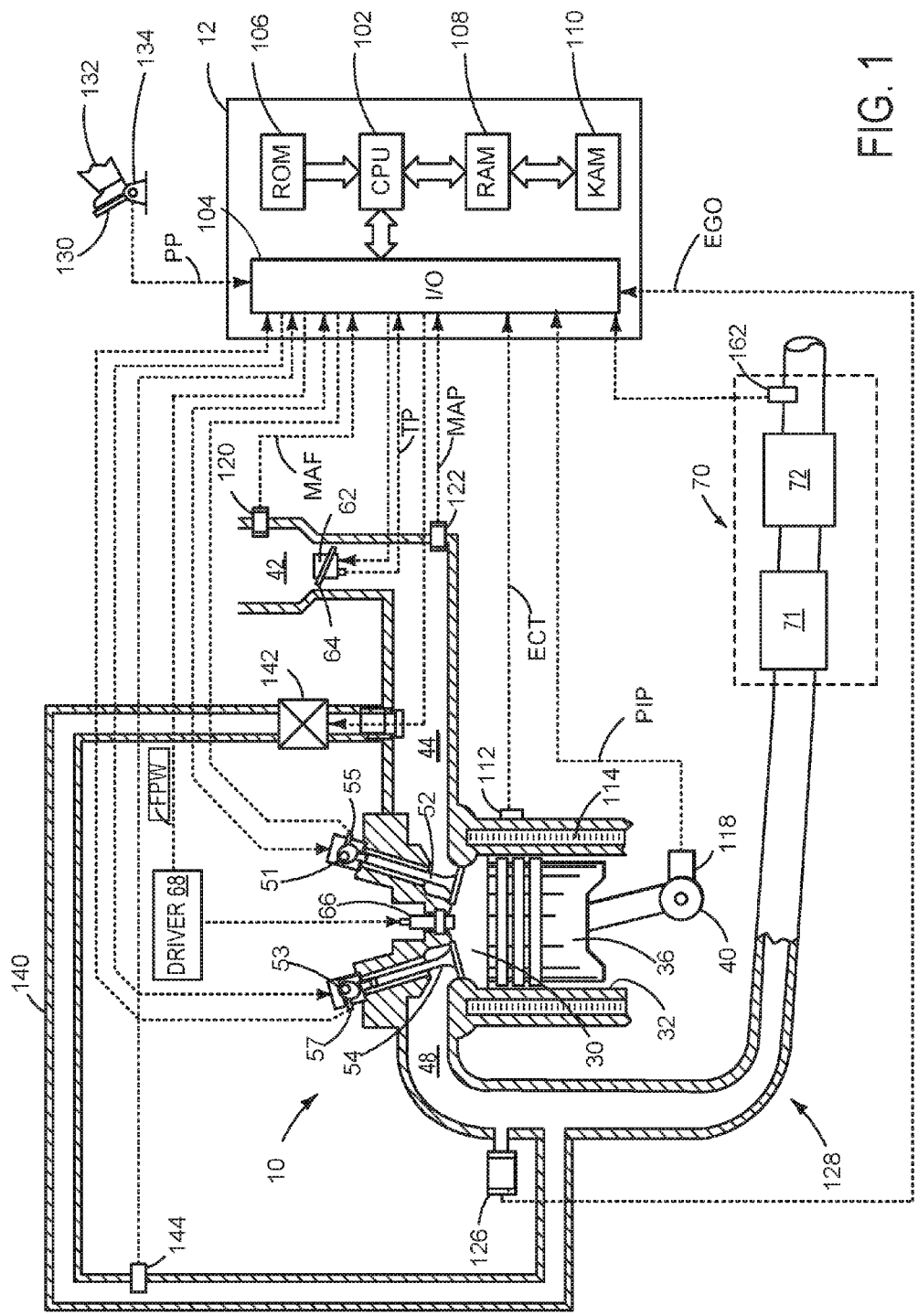
FIG. 1 is a schematic diagram of an engine.
Figure 2:
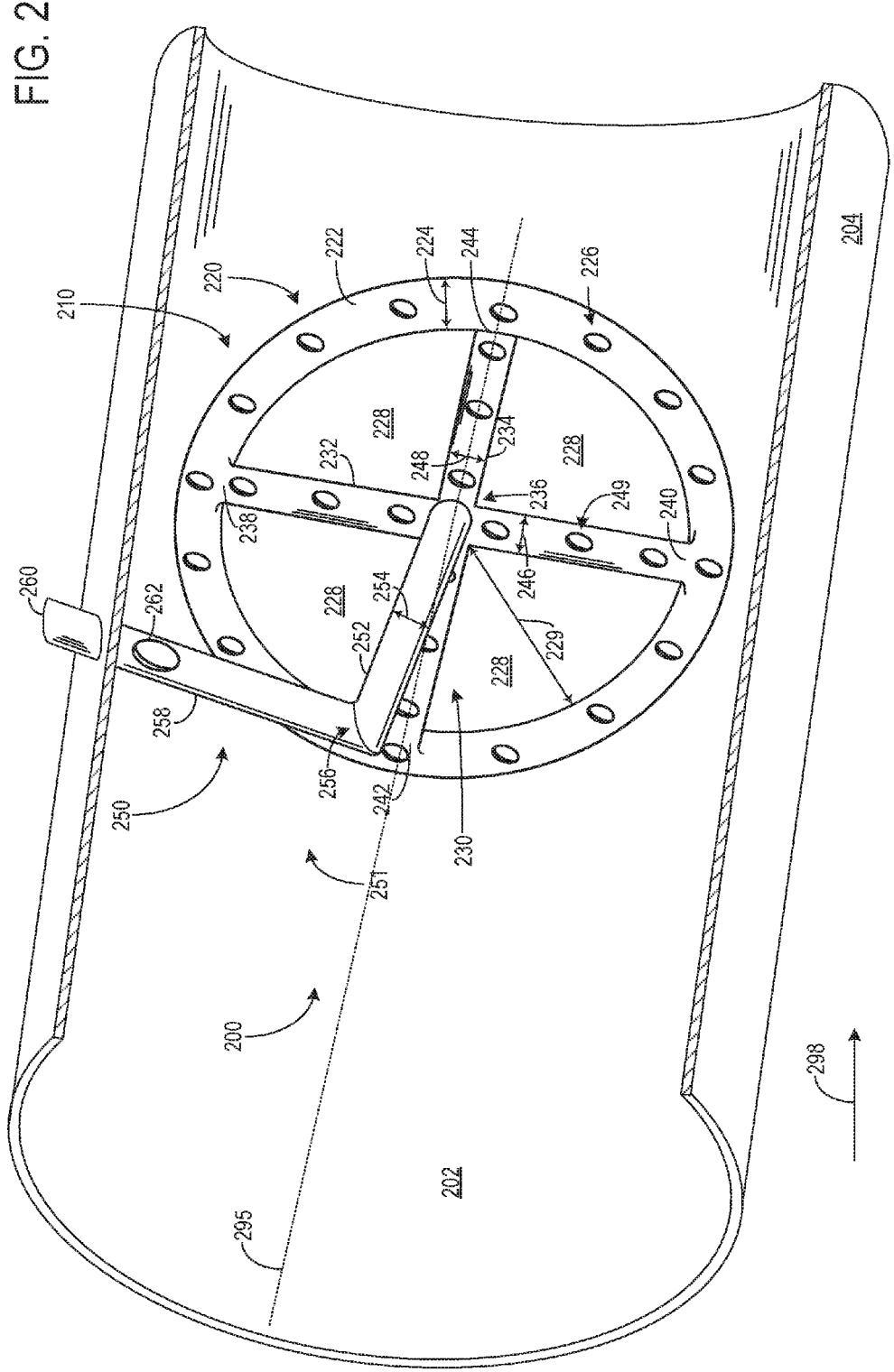
FIG. 2 shows an isometric view of a PM sensor assembly.
Figure 3:
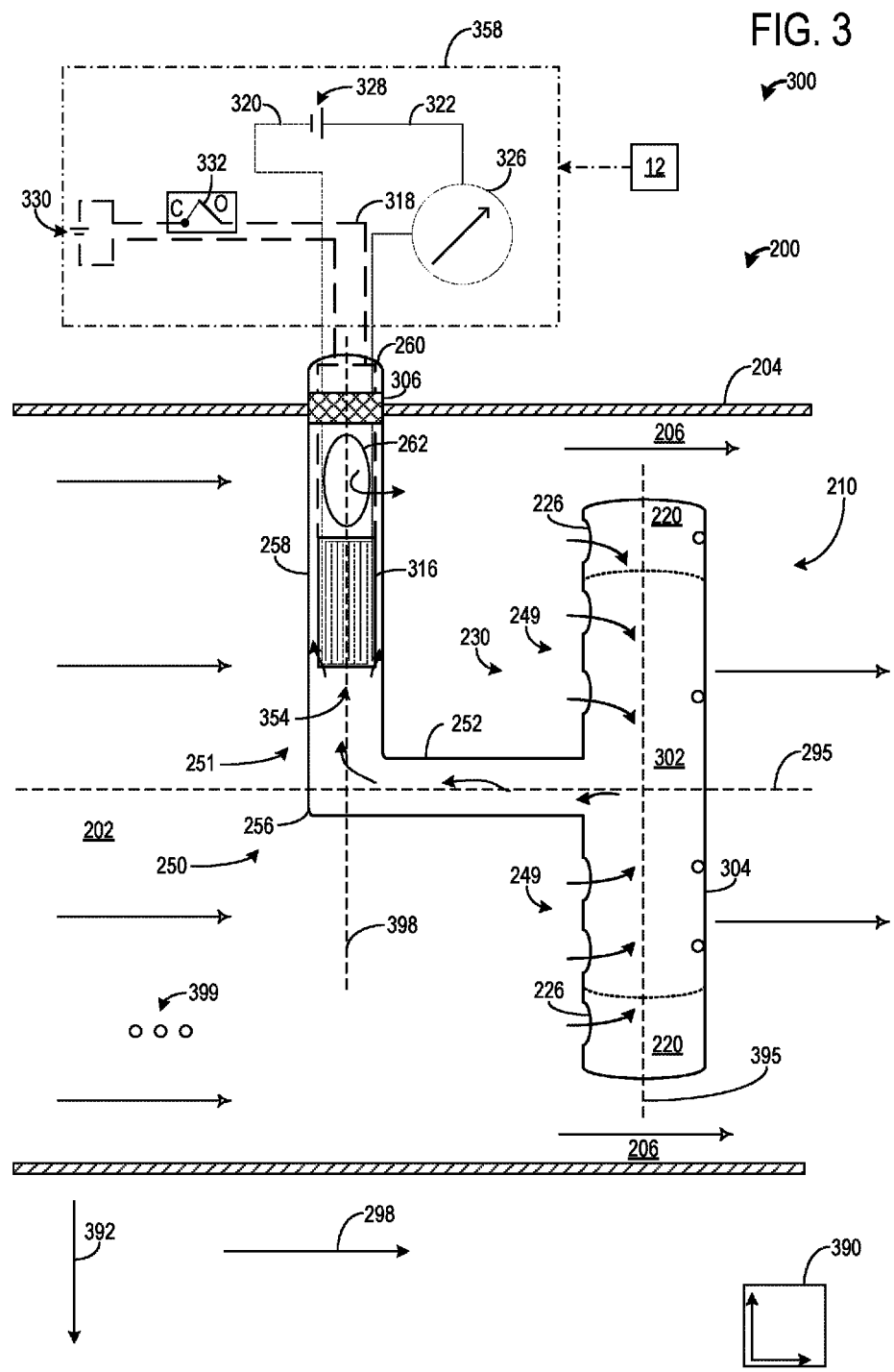
FIG. 3 shows a cross-sectional view of the PM sensor assembly with an example exhaust flow passing through the assembly.

The following description relates to a particulate matter (PM) sensor assembly. The PM sensor assembly may include a pair of intersecting tubes located inside of an outer circular tube. The intersecting tubes may intersect with the circular tube such that an interior space of the intersecting tubes is fluidly coupled to an interior space of the circular tube. The PM sensor assembly may be located in an exhaust passage of an engine downstream of a particulate filter (PF), as shown in FIG. 1. A bent tube is fluidly coupled to the intersecting tubes and the circular tube, allowing exhaust gas to flow in an upstream direction opposite a direction of incoming exhaust flow, as shown in FIG. 2. The PM sensor assembly may conduct exhaust gas toward a soot sensor located in an upper portion of the bent tube, as shown in FIG. 3. A method for determining a condition of the PF based on a detected concentration of soot in exhaust gas downstream of the PF is shown in FIG. 4.

FIGS. 2-3 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber 30 (also termed, cylinder 30) of the engine 10 may include combustion chamber walls 32 with a piston 36 positioned therein. Piston 36 may be coupled to a crankshaft 40 so that reciprocating motion of the piston is translated into rotational motion of the crankshaft 40. Crankshaft 40 may be coupled to at least one drive wheel (not shown) of a vehicle via an intermediate transmission system (not shown). Further, a starter motor (not shown) may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled to the cylinder 30 for injecting fuel directly therein in proportion to the pulse width of signal FPW received from controller 12 via electronic driver 68. In this manner, fuel injector 66 provides what is known as direct injection of fuel into combustion chamber 30. It will also be appreciated that the cylinder 30 may receive fuel from a plurality of injections during a combustion cycle. In other examples, the fuel injector may be mounted in the side of the combustion chamber or in the top of the combustion chamber, for example. Fuel may be delivered to fuel injector 66 by a fuel system (not shown) including a fuel tank, a fuel pump, and a fuel rail.

In the example shown in FIG. 1, engine 10 is configured as a diesel engine that combusts air and diesel fuel through compression ignition. In other embodiments, the engine 10 may combust a different fuel including gasoline, biodiesel, or an alcohol containing fuel blend (e.g., gasoline and ethanol, or gasoline and methanol) through compression ignition and/or spark ignition. Thus, the embodiments described herein may be used in any suitable engine, including but not limited to, diesel and gasoline compression ignition engines, spark ignition engines, direct or port injection engines, etc.

The intake passage 42 may include a throttle 62 having a throttle disc 64. In this particular example, the position of the throttle disc 64 may be varied by controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle disc 64 may be provided to the controller 12 by throttle position signal TP. The intake passage 42 may include a mass air flow sensor 120 and a manifold air pressure sensor 122 for providing respective signals MAF and MAP to the controller 12.

Further, in the disclosed embodiments, an exhaust gas recirculation (EGR) system may route a desired portion of exhaust gas from the exhaust passage 48 to the intake manifold 44 via an EGR passage 140. An amount of EGR provided may be varied by controller 12 via an EGR valve 142. By introducing exhaust gas to the engine 10, the amount of available oxygen for combustion is decreased, thereby reducing combustion flame temperatures and reducing the formation of NOx, for example. As depicted, the EGR system further includes an EGR sensor 144 which may be arranged within the EGR passage 140 and may provide an indication of one or more of pressure, temperature, and concentration of the exhaust gas. Under some conditions, the EGR system may be used to regulate the temperature of the air and fuel mixture within the combustion chamber 30, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 128 includes an exhaust gas sensor 126 coupled to the exhaust passage 48 upstream of an emission control system 70 and the EGR passage 140. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or CO sensor.

Emission control system 70 is shown arranged along exhaust passage 48 downstream of exhaust gas sensor 126. Emission control system 70 may be a selective catalytic reduction (SCR) system, three way catalyst (TWC), NOx trap, various other emission control devices, or combinations thereof. For example, emission control system 70 may include an SCR catalyst 71 and a particulate filter (PF) 72. In some embodiments, PF 72 may be located downstream of the SCR catalyst 71 (as shown in FIG. 1), while in other embodiments, PF 72 may be positioned upstream of the SCR catalyst 71 (not shown in FIG. 1). Emission control system 70 may further include exhaust gas sensor 162. Sensor 162 may be any suitable sensor for providing an indication of a concentration of exhaust gas constituents such as a NOx, NH3, EGO, or a particulate matter (PM) sensor, for example. In some embodiments sensor 162 may be located downstream of PF 72 (as shown in FIG. 1), while in other embodiments, sensor 162 may be positioned upstream of PF 72 (not shown in FIG. 1). Further, it will be appreciated that more than one sensor 162 may be provided along the exhaust passage 48.

As described in more detail with reference to FIG. 2, sensor 162 may be a PM sensor assembly comprising a PM sensor and may measure the mass or concentration of particulate matter downstream of PF 72. For example, sensor 162 may be a soot sensor. Sensor 162 may be operatively coupled to controller 12 and may communicate with controller 12 to indicate a concentration of particulate matter within exhaust exiting PF 72 and flowing through exhaust passage 48. In this way, sensor 162 may detect leakages from PF 72.

Further, in some embodiments, during operation of engine 10, emission control system 70 may be periodically reset by operating at least one cylinder of the engine within a particular air/fuel ratio.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; absolute manifold pressure signal, MAP, from the sensor 122; and exhaust constituent concentration from the exhaust gas sensor 126. Engine speed signal, RPM, may be generated by controller 12 from signal PIP.

The controller 12 receives signals from the various sensors of FIG. 1 (e.g., exhaust gas sensor 162) and employs the various actuators of FIG. 1 to adjust engine operation based on the received signals and instructions stored on a memory of the controller.

As described above, FIG. 1 shows only one cylinder of a multi-cylinder engine, and each cylinder may similarly include its own set of intake/exhaust valves, fuel injector(s), spark plug(s), etc.

FIG. 2 shows an isometric view of a particulate matter (PM) sensor assembly 200. The PM sensor assembly 200 may be used similarly to or with sensor 162 in the embodiment of FIG. 1 and therefore may share common features and/or configurations as those already described for exhaust gas sensor 162. The PM sensor assembly 200 may be configured to measure PM mass and/or concentration in the exhaust gas of an exhaust passage 202 (e.g., exhaust passage 48 in the embodiment of FIG. 1) downstream of a PF (e.g., PF 72). The PM sensor assembly 200 comprises a first stage 210 and a second stage 250. It will be appreciated that PM sensor assembly 200 is shown in simplified form by way of example and that other configurations are possible.

An axis system 390 includes three axes, an x-axis parallel to the horizontal direction, a y-axis parallel to the vertical direction, and a z-axis perpendicular to both the x and y axes. A central axis 295 of the exhaust passage 202, shown by a dashed line, is parallel to the x-axis. Arrow 298 indicates a general direction of exhaust flow and is parallel to the x-axis.

The exhaust passage 202 comprises a tubular exhaust pipe 204 for conducting exhaust gas from an engine (e.g., engine 10 in the embodiment of FIG. 1) to an ambient atmosphere. The exhaust passage 202 may comprise one or more aftertreatment devices located between the engine and the ambient atmosphere for treating exhaust gas. One example aftertreatment device includes a particulate filter (PF) for capturing PM from an exhaust stream. As the PF becomes increasingly loaded with PM, its ability to capture PM may decrease, resulting in increased PM emissions. The PM sensor assembly 200 may determine when the PF becomes fully loaded, where a controller (e.g., controller 12) may signal for an active regeneration of the PF. The active regeneration may include engine adjustments for deliberately increasing an exhaust gas temperature so that PM on the PF may be burned off. Conversely, PM may be burned off the PF via increased exhaust gas temperatures in response to a passive regeneration, which may include engine adjustments increasing the exhaust gas temperature based on a change in engine operation (e.g., increased load). Regenerations may degrade (e.g., crack) the PF, resulting in a PF leakage. The PF leakage may also be measured by the PM sensor assembly. Measuring a regeneration demand and/or degradation of the PF via the PM sensor assembly 200 will be described in greater detail below with respect to FIG. 4.

The PM sensor assembly 200 may be a contiguous device, manufactured as a single piece. The PM sensor assembly may comprise of plastic, metal, silicon, and/or other suitable materials. In one example, the PM sensor assembly may comprise of a material similar to a material of the exhaust pipe 204.

The PM sensor assembly 200 comprises a first stage 210 and a second stage 250. The first stage 210 is physically and fluidly coupled to the second stage 250. The first stage 210 and the second stage 250 comprise a plurality of tubes. The tubes are hollow and cylindrical with substantially equal diameters. The second stage 250 is upstream of the first stage 210. The first stage 210 may readily receive exhaust gas and supply the gas to the second stage 250, where the exhaust gas may flow out of the second stage and back into the exhaust passage 202. The first stage 210 is spaced away from the exhaust pipe 204 and is held in place by the second stage 250, which is physically coupled to the exhaust pipe via a boss.

The first stage 210 includes an outer tube 220 radially spaced away from interior surfaces of the exhaust pipe 204. In some embodiments, a radial space with a radial distance 206 between the outer tube 220 and the exhaust pipe 204 may be substantially uniform around a circumference of the outer tube. In this way, the outer tube 220 is circular. In some embodiments, the radial spaces may not be substantially equal and the outer tube may be oblong, square, rectangular, pentagonal, hexagonal, or other suitable shapes. Substantially equal/uniform/identical may be defined as a deviation between two components being within 1-5% based on manufacturing tolerances.

A body 222 of the outer tube 220 is hollow and cylindrical with an outer tube diameter 224. A cross-section of the body 222 may be substantially circular along the x-axis. An outer common interior passage is located in the body 222 where a volume of the outer common interior passage corresponds to the circumference of the outer tube 220 and an outer tube diameter 224. The outer common interior passage is fluidly coupled to the exhaust passage 202 via a plurality of outer inlets 226, which may readily admit exhaust gas into the body 222. The outer inlets 226 face a direction of incoming exhaust flow (opposite arrow 298) on an upstream surface of the outer tube 220. The outer inlets 226 may be substantially identical to one another in size and shape. As an example, the outer inlets 226 are oblong, however, other suitable shapes for admitting exhaust flow into the common interior passage may be used. The outer inlets 226 may be equidistantly spaced apart from one another such that a distance between a first inlet and a second inlet of the outer inlets 226 is substantially equal to a distance between a third inlet and a fourth inlet of the outer inlets 226. The outer inlets 226 may be oriented in a similar direction. In one example, the outer inlets 226 may be oriented in a vertical direction along the y-axis. In another example, the outer inlet 226 may be oriented to follow a curvature of the outer tube 220.

A bore 228 is located interior to the body 222 and comprises a radius 229. A sum of the radius 229, the outer tube diameter 224, and the radial distance 206 is substantially equal to a smallest radius of the exhaust pipe 204. In this way, exhaust gas may flow through the radial space 206 and/or the bore 228 without flowing into the outer common interior passage of the outer tube 220. Exhaust gas may also contact upstream surfaces of the circular tube 220 located between each of the inlets 226 without flowing into the outer common interior passage. Thus, the outer tube 220 may intercept exhaust gas proximal to the exhaust pipe in the exhaust passage via the outer inlets 226.

The first stage 210 further comprises a pair of intersecting tubes 230, where the intersecting tubes include a first tube 232 and a second tube 234 substantially identical to one another in length, width, and shape. The first tube 232 is parallel to the vertical direction (y-axis) and the second tube 234 is parallel to the horizontal direction (x-axis). The first 232 and second 234 tubes are hollow and cylindrical. A cross-section of the first tube 232 along the x-axis is circular and a cross-section of the second tube 234 along the y-axis is also circular. The first 232 and second 234 tubes fully intersect one another perpendicularly at a midpoint 236 along the length of the tubes corresponding to the central axis 295. The midpoint 236 is one example of an intersection 236. Thus, in this example the intersecting tubes 230 are plus-shaped (cross-shaped). In some examples, the intersecting tubes 230 may be various x-shapes, where the tubes intersect each other obliquely to generate obtuse and acute angles with one another. In the example shown, the bore 228 may be divided into four substantially equal regions configured to allow exhaust to flow therethrough. Each one of the portions is surrounded by a corresponding portion of the first tube 232, the second tubes 234, and the outer tube 220.

Ends of the first 232 and second 234 tubes are physically coupled to the body 222 of the outer tube 220. Specifically, an upper end 238 and a lower end 240 of the first tube 232 are physically coupled to the body 222 along a vertical axis 297. A left end 242 and a right end 244 of the second tube 234 are physically coupled to the body 222 perpendicular to the vertical axis 297. The ends may be physically coupled to the body 222 via adhesives, welds, fusions, and/or other suitable coupling elements.

As mentioned above, the first tube 232 and the second tube 234 are hollow and therefore may comprise an inner common interior passage. The outer common interior passage of the outer tube 220 may extend into the intersecting tubes 230 and be fluidly coupled to the inner common interior passage of the intersecting tubes. Thus, the outer common interior passage refers to an interior volume of the outer tube 220 and the inner common interior passage refers to an interior volume of the first 232 and second 234 tubes. The common interior passage comprises both the outer common interior passage and the inner common interior passage, where the outer common interior passage is fluidly coupled to the inner common interior passage.

A first diameter 246 of the first tube 232 may be substantially equal to a second diameter 248 of the second tube 234. The outer body diameter 224 may be substantially equal to the first 246 and second 248 diameters. Therefore, the common interior passage may be substantially uniform throughout the outer tube 220 and the first 232 and second 234 tubes. In some embodiments, one or more of the outer body diameter 224, the first diameter 246, and the second diameter 248 may be unequal.

The first 232 and second 234 tubes comprise a plurality of inner inlets 249 located on an upstream surface of the tubes. The inner inlets 249 may readily admit exhaust flow into the inner common interior passage. The inner inlets 249 may be substantially identical to one another in size and shape. As an example, the inner inlets 249 may be oblong, however, other suitable shapes may be used for admitting exhaust gas into the inner common interior passage. The inner inlets 249 may be equidistantly spaced apart such that a distance between a first inner inlet and a second inner inlet is substantially equal to a distance between a third inner inlet and a fourth inner inlet of the inner inlets 249. The distance between the inner inlets 249 may be substantially equal to the distance between the outer inlets 226. In some embodiments, the distance between the inner inlets 249 may be greater than or less than the distance between the outer inlets 226.

The second stage 250 comprises a bent tube 251 with a horizontal tube 252 extending along the central axis 295 with a vertical tube 258 extending upward along the y-axis from the horizontal tube 252 to the exhaust pipe 204. The bent tube 251 may be L-shaped, C-shaped, curved, acutely angled, obtusely angled, or other suitable shapes, for example, J-shaped. The horizontal 252 and vertical 258 tubes are hollow and cylindrical.

The second stage 250 is physically coupled to the first stage 210 via the horizontal tube 252. Specifically, the horizontal tube 252 is physically coupled to the first stage 210 at the intersection 236 of the first 232 and second 234 tubes. The horizontal tube 252 is perpendicular to the vertical axis 297. Furthermore, the horizontal tube 252 is perpendicular to both the first 232 and second 234 tubes. The second stage 250 comprises a third diameter 254 which may be substantially equal to one or more of the outer body diameter 224, the first diameter 246, and the second diameter 248. The horizontal tube 252 comprises an interior passage fluidly coupled to the common interior passage at the intersection 236. The horizontal tube 252 extends in an upstream direction opposite arrow 298 and is physically and fluidly coupled to the vertical tube 258 at a bend 256.

The vertical tube 258 extends perpendicularly to the horizontal tube 252 at the bend 256 in the vertical direction. An extreme end (tip) 260 of the vertical tube 258 protrudes through the exhaust pipe 204 outside the exhaust passage 202. In this way, the tip 260 is located in an ambient atmosphere external to the exhaust pipe 204. The vertical tube 258 is physically coupled to the exhaust pipe 204 via one or more welds, adhesives, and fusions at a portion of the second tube between the tip 260 and an outlet 262.

The outlet 262 may be oblong and bigger than the outer 226 and inner 249 inlets. As shown, there is only one outlet 262, where the outlet faces a direction perpendicular to exhaust flow (arrow 298). The outlet 262 may expel exhaust gas received by the common interior passage back to the exhaust passage 202. In some examples, there may be a plurality of outlets similar to the outlet 262. Additionally or alternatively, the outlet 262 may be substantially identical to the outer inlets 226 and the inner inlets 249. Before exhaust gas flows through the outlet 262, a particulate matter (PM) sensor in the vertical tube 258 may capture soot in the exhaust gas. Thus, the vertical tube 258 may herein be referred to as the sensor tube 258. The soot may accumulate onto surfaces of the PM sensor, where the soot may bridge electrodes coupled to the PM sensor. This may indicate a degradation of a PF upstream of the PM sensor assembly 200, as will be described below.

Exhaust gas may enter the common interior passage of the first stage 210 via the outer inlets 226 and the inner inlets 249. Exhaust gas may readily flow through the inlets before turning in a plurality of directions different that its original direction of flow (arrow 298), where the plurality of directions includes a first direction perpendicular to arrow 298 and a second direction oblique to arrow 298. Exhaust gas may flow through the common interior passage (e.g., the outer and inner common interior passages) in the outer tube 220 and the intersecting tubes 230 independent of which inlets (outer inlets 226 or inner inlets 249) it used to enter the first stage 210. The horizontal tube 252 may receive a portion of exhaust gas from the common interior passage and direct the exhaust gas to the sensor tube 258. Large particulate matter and/or water droplets may not enter the horizontal tube 252 due to an increased momentum of the large particulate matter/water droplets compared to small particulate matter. This increased momentum may carry the large particulate matter and/or water droplets to a back wall of the first stage 210. Furthermore, exhaust gas flows in a direction opposite (upstream direction) a direction of exhaust gas in the exhaust passage 202 (arrow 298 pointing in the downstream direction). By reversing the direction of exhaust gas flow, the increased momentum may further inhibit the larger particulates and/or water droplets from entering the horizontal tube 252. The bend 256 alters a direction of exhaust flow by turning the exhaust gas 90° from the upstream direction to the vertical direction. The exhaust gas flows over the PM sensor before flowing through the outlet 262 in a direction perpendicular to the arrow 298.

Thus, a PM sensor assembly comprises a first stage and a second stage. The first stage comprising a pair of intersecting tubes fully intersecting along a midpoint of the tubes. The tubes are physically and fluidly coupled to an outer tube. The outer tube is circular and the intersecting tubes are plus-shaped in one example. The first stage (pair of intersecting tubes and outer tube) are spaced away from and not coupled to an exhaust pipe. The first stage comprises a plurality of outer and inner inlets facing a direction of incoming exhaust flow (upstream direction). A horizontal tube of the second stage is physically and fluidly coupled to the midpoint of the tubes. Thus, inlets of the first stage may intercept exhaust gas from an exhaust passage and deliver the intercepted exhaust gas to the second stage via the horizontal tube along the midpoint of the intersecting tubes. The horizontal tube directs exhaust gas in an upstream direction opposite a direction of exhaust flow in the exhaust passage. The exhaust gas enters a sensor tube in a vertical direction perpendicular to the upstream direction where the exhaust gas may flow over a PM sensor element. An outlet is located vertically above the PM sensor element and may expel the exhaust gas back to the exhaust passage in a direction perpendicular to the direction of exhaust flow in the exhaust passage. In one example, the PM sensor assembly does not comprise additional inlets or other outlets other than those described. In this way, the exhaust gas in the common interior passage of the first stage may not flow back into the exhaust passage without flowing through the outlet of the second stage. Due to a direction of exhaust flow in the horizontal tube, larger particulate matter and/or water droplets may not flow toward the PM sensor due to their increased momentum compared to smaller particulates.

FIG. 3 shows a cross-section 300 of the PM sensor assembly 200 shown in the embodiment of FIG. 2. As such, components previously presented may be similarly number and not re-introduced for reasons of brevity. The PM sensor assembly 200 is shown comprising a PM sensor element 354 configured to intercept PM from an exhaust gas flowing through a second stage 250 of the PM sensor assembly. The PM sensor assembly 200 is arranged along an exhaust passage 202 and physically coupled to an uppermost wall of an exhaust pipe 204 via a boss 306 for a vehicle on the ground, in one example. PM sensor assembly 200 comprises a first stage 210 and a second stage 250. The first stage comprises an outer tube 220 and a pair of intersecting tubes 230. The second stage 250 comprises a bent tube 251 with horizontal 252 and vertical 258 tubes. In the cross-section 300, a first tube 232 of the pair of intersecting tubes 230 is depicted. Thus, a second tube (second tube 234 in the embodiment of FIG. 2) is omitted. However, it should be noted that the second tube may function substantially similarly to the first tube 232 and functional description of the first tube 232 below may also be applied to the second tube.

An axis system 390 is shown comprising two axes, a horizontal axis parallel to the horizontal direction and a vertical axis parallel to the vertical direction. A central axis 295 may be a central axis for both the exhaust pipe 204 and the horizontal tube 252. In this way, the horizontal tube 252 may be aligned with a center of the exhaust pipe 204. In some embodiments, a central axis of the horizontal tube 252 may be misaligned with a central axis of the exhaust passage 202. A central first stage axis 395 of the first stage 210 is shown via a dashed line parallel to the vertical axis. Specifically, the first stage 210 lies in a plane parallel to the first stage axis 395 with an outer tube 220 extending 360° in the plane of the first stage axis about the central axis 295 of the exhaust pipe 204. The second tube may be perpendicular to the first stage axis 395 and the central axis 295. A central sensor tube axis 398 of the sensor tube 258 is shown via a dashed line parallel to the vertical axis upstream of the central axis 295.

The PM sensor element 354 includes a first electrode 320 (depicted by a medium dash line) and a second electrode 322 (depicted by a small dash line) spaced away from each other around the PM sensor element 354. Medium dashes are larger than small dashes. The electrodes are oppositely charged, wherein the first electrode 320 is positively charged and the second electrode 322 is negatively charged. Alternatively, the first electrode 320 may be negatively charged and the second electrode 322 may be positively charged. These electrodes may be manufactured from metals such as platinum, gold, osmium, rhodium, iridium, ruthenium, aluminum, titanium, zirconium, and the like, as well as, oxides, cements, alloys and combinations comprising at least one of the foregoing metals. The electrodes are formed on a sensor substrate 316 that is typically manufactured from highly electrically insulating materials. Possible electrically insulating materials may include oxides such as aluminum, zirconia, yttria, lanthanum oxide, silica, and combinations comprising at least one of the foregoing, or any like material capable of inhibiting electrical communication and providing physical protection for the pair of interdigitated electrodes. Spacing between the two electrodes may be in a range from 10 micrometers to 100 micrometers along features of the sensor substrate 316 with a line width of each electrode being about the same value.

As shown, the sensor substrate 316 is a planar with a rectangular body. However, other embodiments of the sensor substrate 316 may include a circular, concentric, and/or other suitable shapes for capturing PM from the exhaust gas. Flow restrictors may be located in the sensor tube 258, upstream of the sensor substrate 316, for guiding exhaust flow to provide more uniform PM deposition on the sensor substrate. Additionally or alternatively, the sensor substrate 316 may comprise a flow guide for evenly dispersing exhaust gas across a surface of the sensor substrate 316.

The first electrode 320 is connected to a positive terminal of a voltage source 328 of an electric circuit 358. The second electrode 322 is connected to a measurement device 326, which may produce a sensor output, and to a negative terminal of the voltage source 328. The sensor output may be indicative of particulate matter in the engine exhaust gas flow. The electric circuit 358, the voltage source 328, and the measurement device 326 are located away from the exhaust passage 202 by some distance (e.g., less than one meter). Further, the voltage source 328 and the measurement device 326 of the electric circuit 358 may be controlled by a controller, such as controller 12 of FIG. 1, so that particulate matter collected at the PM sensor may be used for diagnosing leaks in a particulate filter (PF) of the exhaust passage 202 (e.g., particulate filter 70 of exhaust passage 48), for example. As such, the measurement device 326 may be any device capable of reading a resistance change across the electrodes, such as a voltmeter. The electrodes may bridge as PM is deposited onto the sensor substrate 316 between the electrodes, as will be described below. A resistance between the electrodes may start to decrease once a deposition of PM spans an entire distance between the electrodes (the electrodes are bridged), which is indicated by a decrease in the voltage measured by the measurement device 326. The controller 12 may be able to determine the resistance between the electrodes as a function of voltage measured by the measurement device 326 and infer a corresponding PM or soot load on the PM sensor element 354. A functioning and/or state of the PF may be determined by monitoring the PM load on the PM sensor element 354.

The PM sensor element 354 also includes a heating element 318, indicated by large dash lines, that is be integrated into the sensor substrate 316. Large dash lines are bigger than medium dash lines. In alternate embodiments, the PM sensor element 354 may not include a heating element 318. The heating element 318 traverses along the central sensor tube axis 396 along a body of the sensor substrate 316. The heating element 318 may comprise, but is not limited to, a temperature sensor, and a heater. Possible materials for the heater and the temperature sensor forming the heating element 318 may include platinum, gold, palladium, and the like; and alloys, oxides, and combinations comprising at least one of the foregoing materials, with platinum/alumina, platinum/palladium, platinum, and palladium. The heating element 318 may be used for regenerating the sensor substrate 316. Specifically, during conditions when the particulate matter load or soot load of the sensor substrate 316 is higher than a threshold load (indicated by a decrease in resistance of one or more of the electrodes), heating element 318 may be operated to burn accumulated soot particles from the sensor substrate 316 by increasing a sensor substrate temperature. During PM sensor regeneration, the controller 12 may provide a voltage to a voltage source 330. In addition, the controller may close the switch 332 (moves to the C-position) for a threshold time to apply the voltage via the voltage source 330 to the heating element 318 in order to raise the temperature of the heating element 318. Subsequently, when the sensor electrodes are sufficiently clean, the controller may open the switch 332 (moves to the O-position) to stop heating the heating element 318 as shown. By intermittently regenerating the PM sensor 200, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter. This information may be muddled by larger particulates and water droplets impinging onto the sensor substrate 316.

As an example, exhaust gas flowing through the exhaust passage 202 may flow adjacent to the exhaust pipe 204, adjacent to the central axis 295, or between the exhaust pipe 204 and the central axis 295. The exhaust gas may comprise large particulates and/or water droplets, as indicated by circles 399. As described above, exhaust gas may flow through radial space 206 or a bore (bore 228 in the embodiment of FIG. 2) without interacting with the PM sensor assembly 200. As described above, the bore may be divided into four equally sized regions due to the intersecting tubes 230. As a result, exhaust gas may flow through any of the four regions of the bore. Conversely, exhaust gas may flow through the outer 226 or the inner 249 inlets in a direction parallel to arrow 298 into a common interior passage 302 before turning at a plurality of angles oblique to the arrow 298. The plurality of angles may include a first angle oblique to arrow 298 and a second angle perpendicular to the arrow 298. Exhaust gas flowing into the common interior passage 302 may comprise large particulates and/or water droplets, which may impinge on a back wall 304 of the first stage 210 due to a greater momentum of the large particulates/water droplets compared to small particulates. The large particulates and water droplets may be at least partially removed during periods of engine operation comprising increased exhaust gas temperatures. Additionally or alternatively, in some embodiments, the first stage 210 may comprise a drainage hole for releasing large particulates and/or water droplets through a lower portion of the outer tube 220.

Exhaust gas comprising smaller particulates may flow through horizontal tube 252. Exhaust gas in the horizontal tube 252 flows in an upstream direction opposite to arrow 298. This combined with the increased momentum of the large particulates/water droplets may further reduce a likelihood of the large particulates/water droplets from entering the horizontal tube 252. Gas in the horizontal tube 252 flows through the bend 256 and up into the sensor tube 258 in a vertical direction 90° to the upstream direction. Thus, exhaust gas in the sensor tube 258 flows against a direction of gravity (arrow 392). PM from the exhaust gas may accumulate onto the sensor substrate 316, where the first electrode 320 and the second electrode 322 may become bridged as the PM load increases beyond a threshold PM load. The resistance of the electrodes is altered as described above. The outlet 262 expels exhaust gas after the exhaust gas interacts with or flows passed the sensor substrate 316.

Exhaust gas flowing out of the outlet 262 flows in a direction perpendicular to arrow 298 in an upper portion of the exhaust passage 202 proximal to the exhaust pipe 204. The combined exhaust flows may flow through a remainder of the exhaust passage 202 and into either an aftertreatment device or an ambient atmosphere.

Thus, the mixer comprises a first stage adapted to receive exhaust flow and a second stage adapted to expel in the exhaust flow. Therefore, exhaust may not enter the second stage without flowing through the first stage. Furthermore, exhaust gas in the first stage may not flow into the exhaust passage without flowing through the second stage. The second stage comprises a PM sensor element for capturing soot and detecting a PM mass and/or concentration in the exhaust gas. The PM sensor element may provide a sensor output indicative of a condition of an upstream particulate filter being fully load or degraded based on a time lapse between electrodes of the PM sensor element being electrically coupled, as will be described below.

Turning now to FIG. 4, a method 400 for determining a particulate load of a PM sensor assembly being greater than a threshold particulate load in order to regenerate the PM sensor is depicted. The method 400 may further depict degradation of a particulate filter in an exhaust passage is degraded based on a time interval between PM sensor regeneration being less than a threshold time interval. Instructions for carrying out method 400 may be executed by a controller (e.g., controller 12 shown in FIG. 1) based on instructions stored on a memory of the controller and in conjunction with signals received from sensors of the engine system, such as the sensors described above with reference to FIG. 1. The controller may employ engine actuators of the engine system to adjust engine operation, according to the methods described below. In one example, the controller may signal an actuator of a fuel injector to inject more fuel to regenerate a fully loaded particulate filter.

Method 400 may be described in reference to components depicted in FIGS. 1, 2, 3, and 4. Specifically, the method 400 may be described with the controller 12, the PF 72, the exhaust gas sensor 162, the PM sensor assembly 200, the first and second electrodes 320 and 322, the heating element 318, and the electric circuit 358 with reference to FIGS. 1, 2, and 3.

Method 400 being at 402 to determine, estimate, and/or measure current engine operating parameters. Current engine operating parameters may include but are not limited to engine load, engine speed, vehicle speed, manifold vacuum, throttle position, exhaust pressure, and an air/fuel ratio.

At 404, the method 400 includes measuring an electrical resistance of the first and second electrodes. In the embodiment of FIG. 4, the first electrode may have a greater resistance than the second electrode. However, it will be appreciated by someone skilled in the art that the second electrode may have a greater resistance than the first electrode.

At 406, the method 400 includes determining if the electrodes are electrically connected (e.g., bridged). The electrodes may become bridged as soot is deposited onto outer surfaces of the sensor substrate between the electrodes. As described above, soot may deposit a flat surface of the sensor substrate and connect the electrodes. As the soot builds up between the first and second electrodes, the soot may touch both electrodes simultaneously and as a result, the electrodes are bridged. When the electrodes are bridged, the resistance of the first electrode may decrease to a resistance of the second electrode due to the conductivity of the soot. If the resistance of the first electrode is greater than the resistance of the second electrode, then the electrodes are not bridged and the method 400 proceeds to 408 to maintain current engine operating parameters and to not regenerate the PM sensor in the PM assembly. Furthermore, a particulate filter (PF) in an exhaust passage may not be leaking or fully loaded with PM (e.g., a PF PM load is less than a threshold PF PM load). Thus, the PF in the exhaust passage may not be regenerated.

If the resistance of the first electrode is substantially equal to the resistance of the second electrode, then the electrodes are bridged and the method 400 proceeds to 410 to activate an electric circuit of the PM sensor to regenerate the PM sensor. The electric circuit may be electrically connected to one or more of the first and second electrodes. Thus, the heating element may be activated by one or more of the first and second electrodes in response to the first and second electrodes being bridged. Alternatively, the heating element may be activated (e.g., switched on) via the controller in response to determining that the first and second electrodes are bridged. The controller may further adjust actuators of the engine in response to activating the electric circuit. For example, the controller may adjust an engine operation to regenerate the particulate filter located in the exhaust passage (e.g., active regeneration). The adjustments may include retarding spark, decreasing an air/fuel ratio of one or more cylinders, increasing the air/fuel ratio of one or more cylinders, and/or increasing a post-injection volume. In this way, regeneration of the PM sensor of the PM sensor assembly may trigger a regeneration of the PF located in the exhaust passage based on the first and second electrodes being bridged.

At 412, the method 400 includes disabling the PM sensor regeneration in response to the first and second electrodes no longer being bridged. The first and second electrodes may no longer be bridged after the heating element regenerates the PM sensor and thus, burns off at least a portion of accumulated soot on the PM sensor. By burning off the soot, the bridge between the first and second electrodes may also be burned and the resistance of the first electrode may become greater than the resistance of the second electrode. The controller may deactivate the electric circuit in response to determining the resistance of the first electrode is greater than the resistance of the second electrode. Alternatively, the first and second electrodes may be electrically coupled to the electric circuit and the circuit may be deactivated by the first and second electrodes in response to the electrodes no longer being bridged.

The regeneration of the PF in the exhaust passage may also be terminated in response to deactivating the heating element. The controller may adjust engine operation back to an optimal engine operation based on a current engine load. Thus, a duration of regeneration for the PM sensor and the PF are substantially equal. Additionally or alternatively, the regeneration of the PF in the exhaust passage may be terminated after a threshold duration has passed after termination of the heating element. For example, the heating element is deactivated and then after the threshold duration has passed, the controller signals actuators of the engine to return to a nominal operation in order to deactivate PF regeneration.

In one example, additionally or alternatively, the regeneration of the PF sensor and the regeneration of the PF may operate for lengths of a first threshold and a second threshold, respectively. In this way, lengths of regeneration of the PF sensor and the PF may be independent. In other words, the first threshold may not be equal to the second threshold. In one embodiment, the first threshold may be less than the second threshold (e.g., the PF is regenerated for a greater length of time compared to the PM sensor). In another embodiment, the first threshold may be greater than the second threshold (e.g., the PF sensor is regenerated for a greater amount of time than the PF).

At 414, the method includes determining a time interval between a last regeneration and a current regeneration of the PM sensor. The last regeneration is defined as a regeneration event that occurred directly before a current regeneration event. The time interval may be calculated based on a duration of time between initiation of the last regeneration and initiation of the current regeneration (e.g., 120 minutes). A time interval may be less than a previous time interval as the PF in the exhaust passage (e.g., particulate filter 72 of FIG. 1) becomes degraded and captures less soot. For example, the particulate filter develops leaks (e.g., cracks), which may allow a greater amount of soot to flow to the PF sensor, resulting in more frequent regenerations of the PF sensor.

At 416, the method 400 determines if the measured time interval is less than a threshold time interval. The threshold time interval may be based on a set threshold (e.g., 200 minutes), a last time interval measured, or a percentage of the last time interval measured (e.g., 50% of the last time interval). Further, the threshold time interval may be based on a threshold that indicates that the time interval is decreasing and the PF sensor has to be regenerated at an increasing rate. Additionally or alternatively, the threshold time interval may be adjusted based on engine operating parameters. For example, the threshold time interval may be decreased as an engine load increases.

If the time interval is not less than the threshold time interval, then the method 400 proceeds to 408 to maintain current engine operation and continue monitoring the electrodes of the PM sensor.

If the time interval is less than the threshold time interval, then the method 400 proceeds to 418 to indicate the PF of the exhaust passage, upstream of the PM sensor assembly, is leaking. Indication of the PF leaking includes adjusting an engine operation and activating an indicator lamp 420 (e.g., in order to indicate to a vehicle operator that the PF is degraded and needs to be replaced).

As an example, a controller (e.g., controller 12) may signal various actuators of an engine (e.g., throttle 62 of engine 10) to limit a torque output of the engine in order to reduce exhaust produced to meet emissions standards. As another example, additionally or alternatively, the method 400 may advance one or more of a spark timing and fuel injection, increase air/fuel ratio, and/or increase EGR. By increasing EGR flow to one or more cylinders of the engine, a combustion mixture temperature(s) is decreased and a volume of fuel injection may be decreased. By doing this, an amount of soot being exhausted from one or more cylinders of the engine may be decreased.

Thus, the method of FIG. 4 provides a method comprising diverting exhaust gas from an exhaust pipe to a PM sensor assembly, where the PM sensor assembly includes a PM sensor with electrodes on a downstream surface and an electric circuit on an upstream surface. The method includes adjusting engine operation based on electrodes of the PM sensor being bridged (e.g., connected). The bridging is based on resistances of the electrodes becoming substantially equal.

In this way, a particulate matter sensor assembly may comprise a first stage configured to receive exhaust gas and a second stage configured to expel exhaust gas. The second stage is upstream of the first stage, allowing larger particulates and/or water droplets to impinge onto a back wall of the first stage without flowing to the second stage. The first stage intercepts exhaust gas from a plurality of regions in an exhaust passage, allowing a PM sensor to sample a greater portion of exhaust flow. This may improve a PM sensor output to provide a more reliable indication of a PM mass or concentration in an exhaust flow downstream of a particulate filter. The technical effect of the particulate matter sensor assembly is to provide a vehicle with a compact, easy to manufacture device for diagnosing a condition of the particulate filter upstream of the assembly.

In a first embodiment, a system comprises two fully intersecting tubes fluidly coupled to an outer circular tube, and where the intersecting and outer tubes are fluidly coupled to a sensor via a bent tube extending in an upstream direction relative to exhaust flow. A first example of the system further comprising where the two fully intersecting tubes intersect one another at a midpoint of each of the tubes. A second example of the system optionally including the first example further includes where the two intersecting tubes and the outer circular tube comprise a plurality of inner and outer inlets. A third example of the system optionally including one or more of the first and second examples further includes where the intersecting tubes and the outer tube are spaced away from an exhaust pipe, and where an upper portion of the bent tube is physically coupled to the exhaust pipe. A fourth example of the system optionally including one or more of the first through third examples further includes where the bent tube comprises a particulate matter sensor with a sensor substrate and electrodes. A fifth example of the system optionally including one or more of the first through fourth examples further includes where in the outer tube comprises a bore, and where the bore is divided into four substantially equal regions by the two intersecting tubes. A sixth example of the system optionally including one or more of the first through fifth examples further includes where the bent tube is L-shaped and physically coupled to the two fully intersecting tubes at an intersection of the intersecting tubes and extends perpendicularly therefrom.

An example of a method comprising flowing exhaust gas from an exhaust passage into a first stage of a particulate matter sensor assembly via a plurality of inlets, directing exhaust gas from the first stage to a second stage of the sensor assembly in a direction opposite a direction of exhaust flow in the exhaust passage, and collecting particulate matter in the exhaust gas onto a soot sensor proximal to an exhaust pipe in the second stage. A first example of the method further includes generating a sensor output signal indicative of particulate matter in the exhaust gas, wherein accumulating particulate matter beyond a threshold load bridges first and second electrodes integrated into a sensor element of the soot sensor. A second example of the method optionally including the first example further includes where bridging the first and second electrodes signals a regeneration of the sensor element.

An example of a particulate matter sensor assembly comprising an outer circular tube radially spaced away from an exhaust pipe and a bore located interior to the outer tube; a pair of intersecting tubes fully intersecting along a midpoint of first and second tubes, and where ends of the first and second tubes are physically coupled to the outer tube, an L-shaped tube comprising a horizontal tube perpendicularly extending from the midpoint in an upstream direction, and a vertical tube extending perpendicularly from the horizontal tube and physically coupled to the exhaust pipe via a boss, and a particulate matter sensor inside the vertical tube configured to capture particulate matter and provide an output based on particulate matter in exhaust gas. A first example of the particulate matter sensor assembly further includes where the outer circular tube comprises a plurality of outer inlets equidistantly spaced apart along an upstream surface of the outer tube, and the pair of intersecting tubes comprising a plurality of inner inlets equidistantly spaced apart along an upstream surface of the first and second tubes. A second example of the particulate matter sensor assembly optionally including the first example further includes where the outer circular tube and the pair of intersecting tubes are hollow and comprise a common interior passage located therein, and where the common interior passage is fluidly coupled to the exhaust passage via the outer and inner inlets. A third example of the particulate matter sensor assembly optionally including one or more of the first and second examples further includes where the plurality of outer and inner inlets face a direction of incoming exhaust flow. A fourth example of the particulate matter sensor assembly optionally including one or more of the first through third examples further includes where the horizontal tube is fluidly coupled to a common interior passage of the outer tube and the intersecting tubes, and where the horizontal tube directs exhaust flow in a direction opposite a direction of exhaust flow in an exhaust passage of the exhaust pipe. A fifth example of the particulate matter sensor assembly optionally including one or more of the first through fourth examples further includes where the vertical tube is fluidly coupled to the horizontal tube and directs exhaust gas in a direction perpendicular to a direction of exhaust flow in the horizontal tube. A sixth example of the particulate matter sensor assembly optionally including one or more of the first through fifth examples further includes where the outer tube and the intersecting tubes are symmetric about a central axis of an exhaust passage of the exhaust pipe. A seventh example of the particulate matter sensor assembly optionally including one or more of the first through sixth examples further includes where the central axis of the exhaust passage aligns with a central axis of the horizontal tube. An eighth example of the particulate matter sensor assembly optionally including one or more of the first through seventh examples further includes where the vertical tube comprises an outlet located above the particulate matter sensor, and where the outlet faces a direction perpendicular to exhaust flow in an exhaust passage. A ninth example of the particulate matter sensor assembly optionally including one or more of the first through eighth examples further includes where the intersecting tubes are located along a plane of the bore and separate the bore into four substantially equally sized regions, with each one of the regions being surround by the first tube, the second tube, and a corresponding portion of the outer tube. A tenth example of the particulate matter sensor assembly optionally including one or more of the first through ninth examples further includes where the outer tube, the intersecting tubes, the horizontal tube, and the vertical tube are cylindrical and comprise substantially identical diameters.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
   two fully intersecting tubes fluidly coupled to an outer circular tube, wherein the intersecting and outer circular tubes are fluidly coupled to a sensor via a bent tube extending in an upstream direction relative to exhaust flow.

2. The system of claim 1, wherein the two fully intersecting tubes intersect one another at a midpoint of each of the tubes.

3. The system of claim 1, wherein the two intersecting tubes and the outer circular tube comprise a plurality of inner and outer inlets.

4. The system of claim 1, wherein the bent tube is L-shaped, and wherein the intersecting tubes and the outer circular tube are spaced away from an exhaust pipe, and where an upper portion of the bent tube is physically coupled to the exhaust pipe.

5. The system of claim 1, wherein the bent tube comprises a particulate matter sensor with a sensor substrate and electrodes.

6. The system of claim 1, wherein the outer circular tube comprises a bore, and where the bore is divided into four substantially equal regions by the two intersecting tubes.

7. The system of claim 1, wherein the bent tube is physically coupled to the two fully intersecting tubes at an intersection of the intersecting tubes and extends perpendicularly therefrom.

8. A method comprising:
   flowing exhaust gas from an exhaust passage into a first stage of a particulate matter sensor assembly via a plurality of inlets;
   directing exhaust gas from the first stage to a horizontal tube of a second stage of the sensor assembly in a direction opposite to a direction of exhaust flow in the exhaust passage, the second stage being upstream of the first stage in the direction of exhaust flow; and
   collecting particulate matter in the exhaust gas onto a soot sensor positioned inside a vertical tube fluidly coupled to the horizontal tube of proximal to an exhaust pipe in the second stage.

9. The method of claim 8, further comprising generating a sensor output signal indicative of particulate matter in the exhaust gas, wherein accumulating particulate matter beyond a threshold load bridges first and second electrodes integrated into a sensor element of the soot sensor.

10. The method of claim 9, wherein the bridging the first and second electrodes signals a regeneration of the sensor element.

11. A particulate matter sensor assembly comprising:
an outer circular tube radially spaced away from an exhaust pipe and a bore located interior to the outer circular tube;
a pair of intersecting tubes fully intersecting along a midpoint of first and second tubes, and where ends of the first and second tubes are physically coupled to the outer circular tube;
an L-shaped tube comprising a horizontal tube perpendicularly extending from the midpoint in an upstream direction, and a vertical tube extending perpendicularly from the horizontal tube and physically coupled to the exhaust pipe via a boss; and
a particulate matter sensor inside the vertical tube configured to capture particulate matter and provide an output based on particulate matter in exhaust gas.

12. The particulate matter sensor assembly of claim 11, wherein the outer circular tube comprises a plurality of outer inlets equidistantly spaced apart along an upstream surface of the outer circular tube, and the pair of intersecting tubes comprising a plurality of inner inlets equidistantly spaced apart along an upstream surface of the first and second tubes.

13. The particulate matter sensor assembly of claim 12, wherein the outer circular tube and the pair of intersecting tubes are hollow and comprise a common interior passage located therein, and where the common interior passage is fluidly coupled to the exhaust passage via the outer and inner inlets.

14. The particulate matter sensor assembly of claim 12, wherein the plurality of outer and inner inlets face a direction of incoming exhaust flow.

15. The particulate matter sensor assembly of claim 11, wherein the horizontal tube is fluidly coupled to a common interior passage of the outer circular tube and the intersecting tubes, and where the horizontal tube directs exhaust flow in a direction opposite a direction of exhaust flow in an exhaust passage of the exhaust pipe to the vertical tube, and where the vertical tube directs exhaust gas in a direction perpendicular to the direction of exhaust flow in the exhaust passage.

16. The particulate matter sensor assembly of claim 11, wherein the outer circular tube and the intersecting tubes are symmetric about a central axis of an exhaust passage of the exhaust pipe.

17. The particulate matter sensor assembly of claim 16, wherein the central axis of the exhaust passage aligns with a central axis of the horizontal tube.

18. The particulate matter sensor assembly of claim 11, wherein the vertical tube comprises an outlet located above the particulate matter sensor, and where the outlet faces a direction perpendicular to exhaust flow in an exhaust passage.

19. The particulate matter sensor assembly of claim 11, wherein the intersecting tubes are located along a plane of the bore and separate the bore into four substantially equally sized regions, with each one of the regions being surround by the first tube, the second tube, and a corresponding portion of the outer circular tube.

20. The particulate matter sensor assembly of claim 11, wherein the outer circular tube, the intersecting tubes, the horizontal tube, and the vertical tube are cylindrical and comprise substantially identical diameters.

* * * * *